(12) United States Patent
Piotrowski et al.

(10) Patent No.: US 8,921,439 B2
(45) Date of Patent: Dec. 30, 2014

(54) MONOHYDROXY CYCLIC PHOSPHONATE SUBSTANTIALLY FREE OF POLYHYDROXY PHOSPHONATE, PROCESS FOR MAKING SAME AND FLAME RETARDANT FLEXIBLE POLYURETHANE FOAM OBTAINED THEREFROM

(75) Inventors: Andrew Piotrowski, Yorktown Heights, NY (US); Anantha N. Desikan, Yorktown Heights, NY (US); Sophia Dashevsky, Monroe Township, NJ (US)

(73) Assignee: ICL-IP America Inc., Ardsley, NY (US)

( * ) Notice: Subject to any disclaimer, the term of this patent is extended or adjusted under 35 U.S.C. 154(b) by 0 days.

(21) Appl. No.: 13/825,196

(22) PCT Filed: Sep. 19, 2011

(86) PCT No.: PCT/US2011/052083
§ 371 (c)(1),
(2), (4) Date: May 21, 2013

(87) PCT Pub. No.: WO2012/040074
PCT Pub. Date: Mar. 29, 2012

(65) Prior Publication Data
US 2013/0237623 A1    Sep. 12, 2013

Related U.S. Application Data

(60) Provisional application No. 61/385,748, filed on Sep. 23, 2010.

(51) Int. Cl.
*C07F 9/40* (2006.01)
*C08K 5/5357* (2006.01)
*C07F 9/6571* (2006.01)

(52) U.S. Cl.
CPC ......... *C08K 5/5357* (2013.01); *C07F 9/657181* (2013.01)
USPC .............. 521/170; 252/609; 558/83

(58) Field of Classification Search
CPC .. C08K 5/5357; C08L 75/08; C07F 9/657181
USPC .............. 521/170; 252/609; 558/83
See application file for complete search history.

(56) References Cited

U.S. PATENT DOCUMENTS

| | | | |
|---|---|---|---|
| 3,470,271 A | 9/1969 | Brotherton et al. | |
| 3,515,776 A | 6/1970 | Baranauckas et al. | |
| 3,600,339 A | 8/1971 | Baranauckas et al. | |
| 3,621,083 A | 11/1971 | Price | |
| 3,699,195 A | 10/1972 | Randall et al. | |
| 3,737,397 A | 6/1973 | Baranauckas et al. | |
| 3,849,368 A | 11/1974 | Anderson et al. | |
| 4,056,547 A | 11/1977 | Tanaka et al. | |
| 4,073,816 A | 2/1978 | Herrmann | |
| 4,564,468 A | 1/1986 | Barda | |
| 4,719,245 A | 1/1988 | Regelman | |
| 4,859,795 A | 8/1989 | Gerdau et al. | |
| 4,880,848 A | 11/1989 | Ghali | |
| 4,935,564 A | 6/1990 | Bunce et al. | |
| 4,977,066 A | 12/1990 | Gersdorf et al. | |
| 4,981,880 A | 1/1991 | Lehmann et al. | |
| 4,981,881 A | 1/1991 | Crivello et al. | |
| 5,106,884 A | 4/1992 | Turner et al. | |
| 5,126,387 A | 6/1992 | Hand | |
| 5,314,928 A | 5/1994 | Verhelst | |
| 5,502,231 A | 3/1996 | Engelhardt et al. | |
| 5,723,704 A | 3/1998 | Demail et al. | |
| 5,910,617 A | 6/1999 | Lecomte et al. | |
| 6,075,158 A | 6/2000 | Hill | |
| 7,067,076 B2 | 6/2006 | Wo et al. | |
| 2007/0112084 A1 | 5/2007 | Hansel et al. | |
| 2009/0281205 A1 | 11/2009 | Piotrowski et al. | |

FOREIGN PATENT DOCUMENTS

| DE | 2442427 A1 | 3/1976 |
|---|---|---|
| GB | 1093893 A | 12/1967 |
| NL | 6502541 A | 8/1965 |

OTHER PUBLICATIONS

Chemical Registry No. 66765-12-6; entered Nov. 16, 1984.
Edward D. Weil et al., "A Survey of Recent Progress in Phosphorus-Based Flame Retardants and Some Mode of Action Studies," Phosphorus, Sulfur and Silicon, 1999, vol. 144-146, pp. 17-20.

*Primary Examiner* — Nathan M Nutter
(74) *Attorney, Agent, or Firm* — Dilworth & Barrese, LLP

(57) ABSTRACT

A monohydroxy cyclic phosphonate substantially free of polyhydroxy phosphonate is employed as a reactive flame retardant in flexible polyurethane.

26 Claims, No Drawings

MONOHYDROXY CYCLIC PHOSPHONATE SUBSTANTIALLY FREE OF POLYHYDROXY PHOSPHONATE, PROCESS FOR MAKING SAME AND FLAME RETARDANT FLEXIBLE POLYURETHANE FOAM OBTAINED THEREFROM

BACKGROUND OF THE INVENTION

Flame retardants play an important role in safeguarding life and property. Their use in flexible polyurethane foam is mandated by a considerable number of regulations specifying fire safety requirements. In addition, the Consumer Products Safety Commission (CPSC) in the United States is considering a regulation for upholstered furniture that would extend a standard similar to or more stringent than the existing California TB 117 standard. Further, recent legislation proposed in California and other states would restrict use of chlorinated and brominated flame retardants. As a result, more efficient and sustainable flame retardants, both halogen-free and halogenated, continue to be sought for use in flexible polyurethane foams.

In flexible polyurethane foams, it is generally not possible to simply substitute one flame retardant for another since flame retardants interact in very specific ways with the polymer matrix and may affect properties of the product. Thus performance is a key factor in substitution. An acceptable flame retardant must not only meet flammability standards but physical properties requirements including resistance to discoloration as well.

In the manufacture of flexible foams, large buns of foam are produced and then set aside to cure. Temperatures within the bun can reach 150° to 180° C. or higher. The insulating properties of the foam maintain this temperature in the interior of the bun for an extended period of time. At such high temperatures some of the foam forming reactions are reversible.

The flame retardant should be able to withstand high temperatures and not contribute to foam degradation usually visible as scorching or charring in the center of the bun.

For low density foams the exotherm generated during the preparation of the foam increases, due to the high amount of added water (resulting in high heat evolution in its reaction with isocyanate to form $CO_2$) needed to lower the density. This makes low density foams particularly sensitive to scorch. High susceptibility to scorch and particularly high flammability of low density foams requires development of robust and highly efficient flame retardants.

Low density flexible polyurethane foams are particularly difficult to flame retard. In a low density flexible polyurethane foam formulation, a small amount of high surface polymer film is surrounded by air facilitating rapid combustion. One solution to this problem has been the use of relatively high amounts of flame retardants to offset their comparatively low flame retardancy effectiveness. This solution, while technically effective in reducing flammability, can have detrimental effects on physical properties of the foam such as flexibility, average cell size, open cell content and/or color stability (resistance to scorch).

At first glance, one possible solution to the problem of imparting required levels of flame retardancy performance to flexible polyurethane foams while retaining acceptable foam properties would be the use of one or more organophosphorus flame retardants having a relatively high content of phosphorus, e.g., at least 10 weight percent phosphorus, for optimum flame retardancy effectiveness. This approach would seem to offer the advantage of achieving required levels of flame retardancy with reduced amounts of flame retardant compound(s) while reducing or minimizing any negative impact on foam properties. Molecules having high phosphorus contents are either oligomers or polymers with multiple phosphorus atoms or small molecules with a single phosphorus atom. Oligomeric and polymeric compounds are usually solids or very viscous liquids and are therefore difficult and/or impractical to use in polyurethane formulations.

However, the use of small high phosphorus content flame retardant molecules is also subject to disadvantages, especially evident in those molecules that are chemically inert relative to the polyurethane foam-forming composition in which they are incorporated, due to their being fairly volatile and as a result, exhibiting a tendency to progressively evaporate from polyurethane foams in which they are physically entrained and/or rapidly escape from the foams ahead of an advancing flame front to which the foams are exposed, both outcomes negatively affecting the flame retardancy effectiveness of these types of molecules.

By way of avoiding the aforementioned drawbacks associated with chemically inert volatile organophosphorus flame retardants, compounds possessing hydroxyl functionality, i.e., so-called reactive flame retardants, have been utilized. During the polyurethane foam-forming reaction, the hydroxyl group(s) of such organophosphorus flame retardant compounds will react with isocyanate groups of the polyisocyanate component(s) of the foam-forming composition thereby chemically anchoring the flame retardants to the foam matrix except when the foam is exposed to flame.

Mixtures of hydroxyl-containing organophosphorus compounds for use as flame retardants in polyurethane foams are known from U.S. Pat. Nos. 3,515,776 and 3,600,339. As a result of the process by which they are made, the mixtures of hydroxyl-containing organophosphorus compounds described in each of these patents contain both a monohydroxy cyclic phosphonate and at least one polyhydroxy phosphonate which may be a cyclic or non-cyclic phosphonate. These mixtures of monohydroxy and polyhydroxy organophosphorus flame retardants, due to the presence of the polyhydroxy phosphonate component(s) therein, will possess a higher hydroxyl number (a measure of the concentration of hydroxyl groups in a substance) than an equal weight amount of monohydroxy cyclic phosphonate which is substantially free of polyhydroxy phosphonate(s). As recognized in US 2007/0112084, high hydroxyl numbers of a reactive flame retardant composition are apt to be disadvantageous in that obtaining a flame retardant polyurethane foam of acceptable properties with them requires a careful balancing between the various components of the foam-forming composition, a requirement that is said to necessitate time-consuming development work. According to US 2007/0112084, the difficulty of obtaining a balanced foam-forming composition becomes less as the hydroxyl number of the flame retardant compound or mixture of compounds decreases and as the level of flame retardant required for satisfactory flame retardancy performance becomes smaller. For this reason, US 2007/0112084 gives preference to reactive flame retardants having a low hydroxyl number and/or high activity. Included within the genus of monohydroxy phosphonate flame retardant compounds described in US 2007/0112084 are those in which a hydroxyalkyl group of at least two carbon atoms is directly bonded to the phosphorus atom of a six-membered ring.

It has now been discovered that a particular class of monohydroxy cyclic phosphonates which is substantially free of polyhydroxy phosphonate, and featuring a single hydroxylalkyl group bonded to a ring carbon atom in contrast to a ring phosphorus atom as in the flame retardants of US 2007/

0112084, provides flexible polyurethane foams meeting the strictest standards of flame retardancy performance while still exhibiting industry-acceptable foam properties.

BRIEF SUMMARY OF THE INVENTION

In accordance with the invention, there is provided a monohydroxy cyclic phosphonate, suitable for use as a flame retardant for flexible polyurethane foam, of general formula (I):

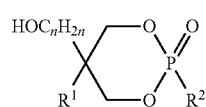
(I)

wherein $R^1$ and $R^2$ each independently is an alkyl, alkenyl, aryl, alkaryl, aralkyl or alkoxy group of up to 10 carbon atoms, a —$CH_2CH_2OR^3$ group, a —$CH_2CH_2OC(\!\!=\!\!O)R^3$ group or a —$CH_2CH_2C(\!\!=\!\!O)OR^3$ group in which each $R^3$ independently is an alkyl, alkenyl, aryl, alkaryl, aralkyl or alkoxy group of up to 10 carbon atoms, and n is 1 to 8, monohydroxy cyclic phosphonate (I) being substantially free of polyhydroxy phosphonate and containing a phosphorus content of 8 weight percent or greater.

Further in accordance with the invention, there is provided a process for making monohydroxy cyclic phosphonate (I) which avoids the coproduction of polyhydroxy phosphonate(s), the process comprising reacting at least one diaryl phosphonate of general formula (III):

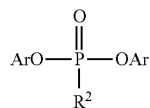
(III)

wherein each Ar independently is an aryl or alkaryl group of from 6 to 10 carbon atoms and $R^2$ has one of the aforestated meanings, with at least one trihydroxy alcohol of general formula (IV):

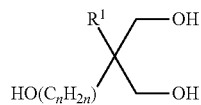
(IV)

wherein $R^1$ has one of the aforestated meanings and n is 1 to 8 to provide monohydroxy cyclic phosphonate (I).

Still further in accordance with the invention, there is provided a flame retardant flexible polyurethane foam obtained from a flexible polyurethane foam-forming composition containing a flame retardant-effective amount of a flame retardant composition containing at least one monohydroxy cyclic phosphonate (I), supra, alone or in combination with one or more other phosphorus-containing flame retardant compounds which are not polyhydroxy phosphonates.

The expression "polyurethane foam" shall be understood herein to include polyurethane foam per se as well as polyisocyanurate foam, polyurethane-isocyanurate foam, polyurea foam, polyurethane-urea foam and polyurethane-isocyanurate-urea foam.

The term "flexible" as it applies to the flame retardant polyurethane foam herein shall be understood to include flexible and semi-flexible foams.

While the monohydroxy cyclic phosphonate flame retardant (I) and its admixtures with dicyclic phosphonate (II) and/or one or more other phosphorus-containing flame retardants (excepting the aforementioned polyhydroxy phosphonate flame retardants) including any of those described infra are especially advantageous for use in the manufacture of flexible polyurethane foams, it will be understood that these flame retardants are also useful for making rigid, microcellular, predominantly open-cell and/or predominantly closed-cell fire retardant polyurethane foams of all types.

DETAILED DESCRIPTION OF THE INVENTION

In monohydroxy cyclic phosphonate (I), $R^1$ is preferably methyl, ethyl, n-propyl, isopropyl, n-butyl, sec-butyl, tert-butyl or phenyl, $R^2$ is preferably methyl, ethyl, propyl, isopropyl, n-butyl, sec-butyl, tert-butyl, phenyl, benzyl, o-tolyl, m-tolyl or p-toyl, or allyl and n is preferably 1 to 4 and more preferably 1.

Examples of some useful monohydroxy cyclic phosphonates (I) include:

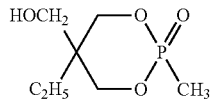

1,3,2-dioxaphosphorinane-5-methanol, 5-ethyl-2-(2-methyl)-, 2-oxide

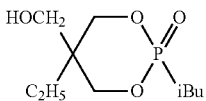

1,3,2-dioxaphosphorinane-5-methanol, 5-ethyl-2-(2-methylpropyl)-, 2-oxide

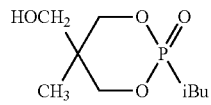

1,3,2-dioxaphosphorinane-5-methanol, 5-methyl-2-(2-methylpropyl)-, 2-oxide

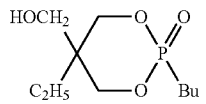

1,3,2-dioxaphosphorinane-5-methanol, 5-ethyl-2-(n-butyl)-, 2-oxide

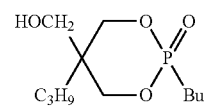

1,3,2-dioxaphosphorinane-5-methanol, 5-propyl-2-(n-butyl)-, 2-oxide

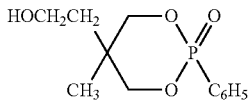

1,3,2-dioxaphosphorinane-5-ethanol, 5-methyl-2-phenyl-, 2-oxide

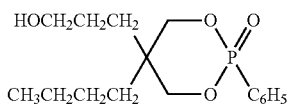

1,3,2-dioxaphosphorinane-5-propanol, 5-butyl-2-phenyl-, 2-oxide

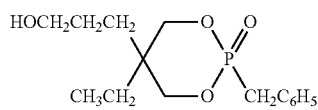

1,3,2-dioxaphosphorinane-5-propanol, 5-ethyl-2-benzyl-, 2-oxide

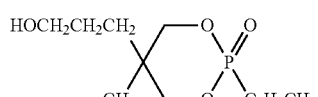

1,3,2-dioxaphosphorinane-5-propanol, 5-methyl-2-p-tolyl-, 2-oxide

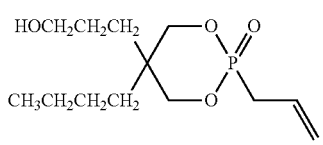

1,3,2-dioxaphosphorinane-5-propanol, 5-butyl-2-(allyl)-, 2-oxide

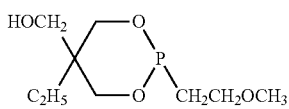

1,3,2-dioxaphosphorinane-5-methanol, 5-ethyl-2-methoxyethyl-, 2-oxide

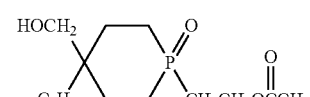

1,3,2-dioxaphosphorinane-5-methanol, 5-ethyl-2-acetoxyethyl-, 2-oxide

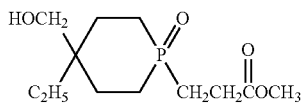

1,3,2-dioxaphosphorinane-5-methanol, 5-ethyl-2-methoxypropanoxycarbonyl-, 2-oxide

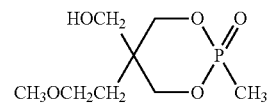

1,3,2-dioxaphosphorinane-5-methanol, 5-methoxyethyl-2-(2-methyl)-, 2-oxide

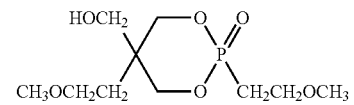

1,3,2-dioxaphosphorinane-5-methanol, 2,5-dimethoxyethyl-, 2-oxide and their mixtures.

In general, the monohydroxy cyclic phosphonate (I) of the invention can be prepared by reacting at least one diaryl phosphonate of general formula (III):

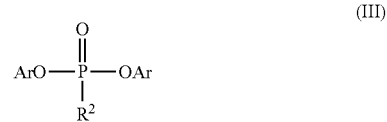

wherein each Ar independently is an aryl or alkaryl group of from 6 to 10 carbon atoms, preferably phenyl, and $R^2$ has one of the aforestated meanings, preferably methyl, ethyl, propyl, isopropyl, n-butyl, sec-butyl, tert-butyl or phenyl, with at least one trihydroxy alcohol of the general formula (IV):

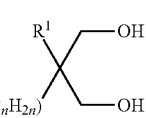

wherein $R^1$ and n each has one of the aforestated meanings with $R^1$ preferably being methyl, ethyl, n-propyl, isopropyl, n-butyl, sec-butyl, tert-butyl or phenyl and n preferably being 1-4 and more preferably 1.

Examples of useful diaryl phosphonate (III) reactants include diphenylmethylphosphonate, diphenylphenylphosphonate, diphenylethylphosphonate, diphenylbutylphosphonate, diphenyl-iso-butylphosphonate and mixtures thereof.

Examples of useful trihydroxy alcohol (IV) reactants include 1,3-propanediol, 2-ethyl-2-(hydroxymethyl), 1,3-propanediol, 2-phenyl-2-(hydroxymethyl), 1,3-propanediol, 2-ethyl-2-(hydroxybutyl), $CH_3OCH_2CH_2C(CH_2OH)_3$, $CH_3OCH_2CH_2C(CH_2OH)_2CH_2CH_2OH$, $CH_3C(=O)$ $OCH_2CH_2C(CH_2OH)_3$, $CH_3C(=O)OCH_2CH_2C(CH_2OH)_2$ $CH_2CH_2OH$, $CH_3OC(=O)CH_2CH_2C(CH_2OH)_3$, $CH_3OC(=O)CH_2CH_2C(CH_2OH)_2CH_2CH_2OH$ and mixtures thereof.

In carrying out the foregoing reaction of diaryl phosphonate (III) with trihydroxy alcohol (IV), reaction conditions generally providing good results include a molar ratio of (III) to (IV) of 1, preferably 1:1.1 and more preferably 1:1.2, a temperature of from 100 to 180° C. and preferably from 130 to 150° C., at ambient pressure (although elevated or reduced pressure can be used if needed) in the presence of a suitable catalyst, e.g., a basic catalyst such as KF, $Ca(OH)_2$ or potassium phenolate, optionally, one or more inert organic solvents capable of dissolving both the reactants and the reaction product(s), e.g., a polar aprotic solvent such as bis(2-methoxyethyl)ether (diglyme), dimethylformamide, dimethyl sulfoxide and chlorobenzene, preferably under an inert atmosphere such as dry nitrogen, and for a period of from 10 minutes to 3 hours and preferably from 30 minutes to 1 hour. Following the reaction, by-product ArOH may be removed under vacuum and, if desired, catalyst as well employing any known or conventional procedures.

The foregoing reaction of diaryl phosphonate (III) with trihydroxy alcohol (IV), in addition to producing monohydroxy cyclic phosphonate (I) and by-product ArOH (which can be recovered, if desired, and utilized for the production of diaryl phosphonate (III)), has been found also to co-produce generally minor amounts, e.g., not exceeding about 45 weight percent of total phosphonate product, of dicyclic phosphonate of general formula (II):

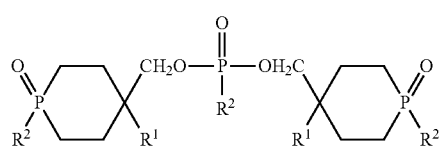

wherein $R^1$ and $R^2$ each independently has one of the aforestated meanings.

The reaction of diaryl phosphonate (III) with trihydroxy alcohol (IV) to provide the foregoing mixture of monohydroxy cyclic phosphonate (I) and co-produced dicyclic phosphonate (II) can be considered to proceed as follows (illustrated for the case where n=1):

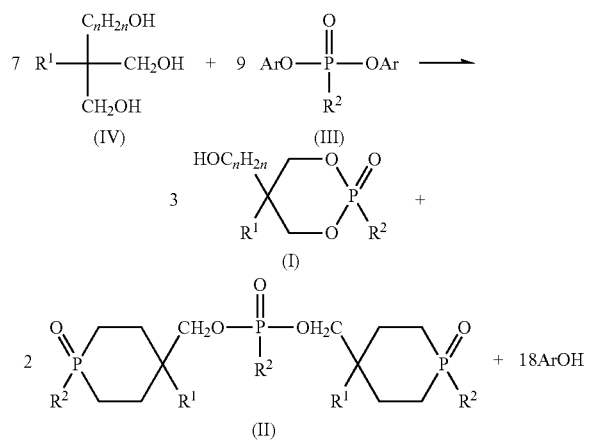

In the particular case of monohydroxy cyclic phosphonate (I) wherein $R^2$ is a $-CH_2CH_2OR^3$ group, $-CH_2CH_2OC(=O)R^3$ or a $-CH_2CH_2C(=O)OR^3$ group, the phosphonate can be readily prepared by reacting a trihydroxy alcohol of formula (IV), supra, with a dialkyl phosphite (V) of the general formula $(R^4O)_2P(=O)H$ in which each $R^4$ independently is an alkyl group of from 1 to 4 carbon atoms, to provide a mixture of monohydroxy cyclic phosphite (VI) and oligomeric cyclic phosphite (VII), and reacting the resulting product mixture, and advantageously only the phosphite (VI) product which has previously been isolated from the product mixture, e.g., by distillation, in substantially pure form, with an acrylate ester, vinyl ester or vinyl ether, to provide the corresponding phosphonate (I). This sequence of reactions, illustrated for diethylphosphite and the reaction of subsequently isolated monohydroxy cyclic phosphite (VII) (it being understood that reaction of phosphite (VII) with acrylate or vinyl ester will also provide useful flame retardant(s)), can be considered to proceed as follows:

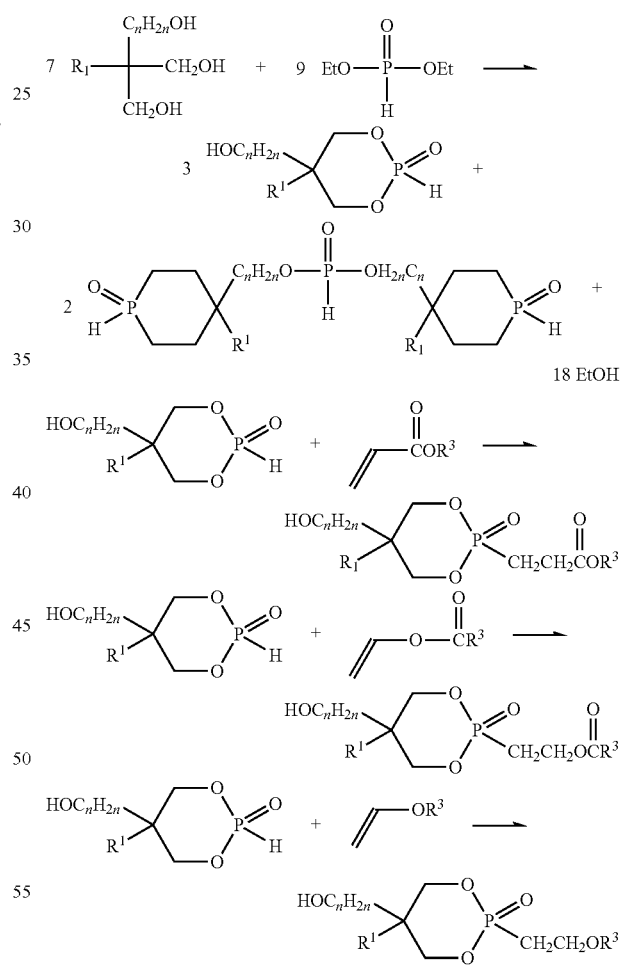

Dicyclic phosphonates (II) and their use as flame retardants for flexible polyurethane foams are known. If desired, co-produced dicyclic phosphonate (II) can be separated from monohydroxy cyclic phosphonate (I) by any of several known and conventional procedures, e.g., distillation, or, if desired, can be allowed to remain in admixture with monohydroxy cyclic phosphonate (I) where it will contribute to overall flame retardancy performance.

Monohydroxy cyclic phosphonate (I), either substantially pure or in admixture with co-produced dicyclic phosphonate (II), can be combined with one or more other flame retardant compounds other than those containing two or more hydroxyl groups such as the polyhydroxy-containing phosphonates disclosed in U.S. Pat. Nos. 3,515,776 and 3,600,339 mentioned above. Examples of such additional useful flame retardants include organophosphorus flame retardants such as 4-tert-butylphenyl diphenyl phosphate (CAS 981-40-8), tert-butylphenyl diphenyl phosphate (CAS 56803-37-3) and iso-propylphenyl diphenyl phosphate (CAS 28108-99-8).

In general, the phosphorus content of monohydroxy cyclic phosphonate (I), its mixtures and combinations of monohydroxy cyclic phosphonate(s) (I) with one or more other phosphorus-containing flame retardants such as any of those previously mentioned will be 8.0 weight percent or greater, preferably 9.0 weight percent or greater and more preferably 10.0 weight percent or greater based on the entire amount of phosphorus-containing compound(s) present.

The amount of monohydroxy cyclic phosphonate (I) to be incorporated in a flexible polyurethane foam, either by itself or in combination with one or more other phosphorus-containing flame retardants (other than those of the polyhydroxy variety), will be at least that amount required to impart effective flame retardant properties to the foam criteria for which may in some cases be established or influenced by government regulation or industry standards. The amounts of a specific flame retardant additive that are effective for a specific flexible polyurethane foam-forming composition can be readily determined employing routine testing such as that described infra.

In general, substantially pure monohydroxy cyclic phosphonate (I) can be incorporated in a flexible polyurethane foam-forming composition to provide effective fire retardant properties in the product foam at a level of from 2 to 20, preferably from 3 to 15, and more preferably from 4 to 12, weight parts per 100 weight parts of the polyol of the composition. Admixtures of monohydroxy cyclic phosphonate (I) with dicyclic phosphonate (II) and/or one or more other non-polyhydroxy type phosphorus-containing flame retardants typically containing from 55 to 80 weight percent (I) with the balance being (II) and/or other phosphorus-containing flame retardant(s) can be incorporated in a flexible polyurethane foam-forming composition at a level of from 4 to 20, preferably from 6 to 18, and more preferably from 8 to 16, weight parts per 100 parts of the total polyol content of the foam-forming composition for effective fire retardant performance.

Further in accordance with the present invention, there is provided a flexible polyurethane foam-forming composition which, under flexible polyurethane foam-forming conditions, provides a flame-retarded flexible polyurethane foam, the composition comprising:
  a) at least one polyol;
  b) at least one polyisocyanate;
  c) at least one blowing agent;
  d) at least one catalyst for the polyurethane foam-forming reaction;
  e) at least one monohydroxy cyclic phosphonate (I), supra; and,
  f) optionally, one or more other components.

Component (e) of the foregoing polyurethane foam-forming composition is described in detail, supra.

Individual components (a)-(d) and (f) thereof will now be described.

(a) Polyol

Examples of polyols which can be used include those commonly used in the production of flexible polyurethane foams such as polyether polyols, polyester polyols and polymer polyols.

Examples of polyether polyols include those with a hydroxyl value of from about 25 to about 70 KOHmg/g which are obtained by the random or block addition of alkylene oxides such as ethylene oxide and propylene oxide to polyfunctional polyols, amine compounds, and the like. Examples of polyfunctional polyols include glycols such as ethylene glycol and propylene glycol; triols such as glycerol and trimethylolpropane; polyols such as pentaerythritol, sorbitol and sucrose. Examples of amine compounds include ammonia, triethanolamine, ethylene diamine, diethylene triamine, aminoethyl piperazine and aniline.

Polyester polyols are compounds having terminal hydroxyl groups obtained by the polycondensation of polyfunctional carboxylic acids and polyfunctional hydroxyl compounds or the ring-opening self-condensation polymerizations of a lactone. The polyester polyols preferably have a number average molecular weight of from about 500 to about 10,000, and more preferably from about 1000 to about 5000. Examples of polyfunctional carboxylic acids include adipic acid, phthalic acid, succinic acid, azelaic acid and sebacic acid. Examples of polyfunctional hydroxy compounds include glycols such as ethylene glycol, propylene glycol, butanediol and diethylene glycol, and polyhydric alcohols such as glycerol, trimethylol propane and pentaerythritol. Examples of lactones include gamma-butyrolactone and epsilon-caprolactone.

Polymer polyols can be obtained by mixing a polyether polyol and an ethylenically unsaturated monomer, and, when necessary, adding chain transfer agents, dispersion stabilizers, and the like, to bring about the radical polymerization of the ethylenically unsaturated monomer in the presence of a radical initiator. Examples of ethylenically unsaturated monomers include monomers containing the cyano group such as acrylonitrile and methacrylonitrile; (meth)acrylic esters such as methyl(meth)acrylate, butyl(meth)acrylate, stearyl(meth)acrylate, hydroxyethyl(meth)acrylate, dimethylaminoethyl(meth)acrylate and dimethylaminopropyl (meth)acrylate; monomers containing carboxyl group such as acrylic acid, methacrylic acid, itaconic acid, maleic acid and fumaric acid; acid anhydride monomers such as maleic anhydride and itaconic anhydride; hydrocarbon compounds such as butadiene, isoprene and 1,4-pentadiene; aromatic hydrocarbon compounds such as styrene, alpha-methyl styrene, phenylstyrene and chlorostyrene; halogen-containing monomers such as vinyl chloride and vinylidene chloride; vinyl ethers such as vinyl ethyl ether and vinyl butyl ether; vinyl ketones such as vinyl ethyl ketone; vinyl esters such as vinyl acetate; acrylamides such as acrylamide, N,N-dimethylacrylamide, N-isopropylamide, N,N-dimethylaminopropyl acrylamide and methylene bisacrylamide; and methacrylamides such as N,N-dimethyl methacrylamide. Such ethylenically unsaturated monomers can be used alone or in combinations of two or more.

The aforementioned polyol components can be used alone or in combinations of two or more depending on the properties required of the flexible polyurethane foam that is to be prepared.

For example, a flexible polyurethane foam with high elasticity can be obtained when the aforementioned polyether polyol and polymer polyol are used in a proportion, based on the combined weight of the two, of from about 30 to about 90 weight percent of the former and from about 70 to about 10 weight percent of the latter, and preferably from about 40 to about 80 weight percent of the former and from about 60 to about 20 weight percent of the latter.

(b) Polyisocyanate

Examples of polyisocyanates which can be used include those having two or more isocyanate groups which have heretofore been used for making flexible polyurethane foams. Examples of such polyisocyanate compounds include aromatic polyisocyanates, aliphatic polyisocyanates and alicyclic polyisocyanates, as well as mixtures of two or more of such polyisocyanates, and modified polyisocyanates obtained by the modification of such polyisocyanates. Specific examples of such polyisocyanates are tolylene diisocyanate, diphenylmethane diisocyanate, polymethylene polyphenylene polyisocyanate (crude MDI), xylylene diisocyanate, isophorone diisocyanate and hexamethylene diisocyanate; and modified products of such polyisocyanates, such as carbodiimide-modified products, biuret-modified products, dimers and trimers. Prepolymers with terminal isocyanate groups obtained from such polyisocyanates and active hydrogen-containing compounds can also be used.

(c) Blowing Agent

As the blowing agent in the flexible polyurethane foam-forming composition of the present invention, known blowing agents of both the chemical and physical blowing agent variety heretofore used in such compositions are suitably selected according to the properties required of the foamed product.

Water is a typical example of a chemical blowing agent. Examples of suitable physical blowing agent include hydrofluorocarbons, methylene chloride, n-butane, isobutane, n-pentane, isopentane, dimethyl ether, acetone, carbon dioxide, and the like. Depending on the desired density and other properties of the foamed polyurethane, these and other blowing agents can be used alone or in combinations of two or more in a manner known in the art.

The amount of blowing agent to be used is not particularly limited but will ordinarily range from about 0.1 to about 40 parts by weight per 100 parts by weight of the polyol component of the foam-forming composition.

(d) Catalyst

The flexible polyurethane foam-forming composition herein can contain any of the catalysts, and combination of catalysts, heretofore known or used for the production of polyurethane foams. Examples of useful catalysts include sodium hydroxide, sodium acetate, tertiary amines or materials which generate tertiary amines such as trimethylamine, triethylene diamine, N-methyl morpholine, N,N-dimethyl cyclohexylamine, and N,N-dimethyl aminoethanol. Also applicable are metal compounds such as hydrocarbon tin alkyl carboxylates, dibutyl tin diacetate, dibutyl tin dioctoate dibutyl tin dilaurate and stannous octoate; as well as other compounds intended to promote trimerization of the polyisocyanate such as, 2,4,6-tris(N,N-dimethylamino-methyl)phenol, 1,3,5-tris(N,N-dimethyl-3-aminopropyl)-S-hexahydrotriazine, potassium octoate, potassium acetate and catalysts such as DABCO TMR® and POLYCAT 43®.

Suitable flexible polyurethane-isocyanurate foam-forming compositions are disclosed in, e.g., U.S. Pat. Nos. 4,719,245 and 4,981,880, the entire contents of which are incorporated by reference herein. Suitable flexible polyurea foam-forming compositions are disclosed in, e.g., U.S. Pat. No. 5,106,884, the entire contents of which are incorporated by reference herein. Suitable flexible polyurethane-urea foam-forming compositions are disclosed in, e.g., U.S. Pat. No. 5,314,928, the entire contents of which are incorporated by reference herein. Suitable semiflexible polyurethane-isocyanurate-urea foams are disclosed in, e.g., U.S. Pat. No. 4,880,848, the entire contents of which are incorporated by reference herein.

Monohydroxy cyclic phosphonate (I) flame retardant will be incorporated in the flexible polyurethane foam-forming composition herein in amounts which will impart acceptable flame retardant characteristics to the foam formed therefrom. In general, these amounts can vary from about 2 to about 30, and preferably from about 6 to about 20, weight parts per 100 weight parts of total isocyanate-reactive polymer(s) in the foam-forming composition.

The following examples are illustrative of monohydroxy cyclic phosphonate (I), its preparation and flame retardant flexible polyurethane foams prepared therefrom.

Example 1

This example illustrates the preparation and isolation of substantially pure Compound (1):

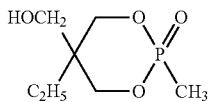

1,3,2-dioxaphosphorinane-5-methanol, 5-ethyl-2-(2-methyl)-, 2-oxide

A 2.5 liter Mettler Toledo RC1 reactor was filled with 1200 g of diphenyl methylphosphonate (DPMP) and 700 g trimethylol propane (0.93 to 1 molar ratio). The contents of the reactor were heated to 110° C. and residual moisture was removed under vacuum. The reactor contents were then filled with nitrogen and 8.7 g pulverized KF was added as catalyst. Some exotherm was observed and thereafter the reactor contents were heated to 180° C. over a period of 30 minutes and maintained at this temperature for 30 minutes. A sample of reaction product was taken and NMR analysis indicated that all of the DPMP was consumed. Vacuum was then applied and by-product phenol stripped under reduced pressure allowing the reactor contents to cool to 130° C. Residual product contained approximately 70% by weight of Compound (1). This preparation was repeated and the combined 2 batches were dissolved in a mixture of 1 liter of methylene chloride and 300 ml of toluene. To remove residual catalyst, the 24 g of Ca(OH)$_2$ and 10 g of water were added to the combined batches. The mixture was stirred for 2 hours at room temperature, dried over Mg(SO$_4$)$_2$ and filtered. The mixture was then gradually heated to 150° C. to remove residual solvent. Compound (1) (670 g) was isolated from Compound 2 using wiped film evaporator at 170° C. and 20 millibar pressure starting with 1100 g of the solvent and catalyst free reaction mixture. NMR analysis indicated 99% purity. The hydroxyl number of the substantially pure Compound (1) is about 288 and its phosphorus content approximately 15.9 weight percent.

Example 2

This example illustrates the preparation of Compound (1) without its isolation from co-produced dicyclic phosphonate Compound (2).

A mixture of 1,1,1-tris(hydroxymethyl)propane (238 g, 1.8 mol, 1 equivalent) and diphenyl methylphosphonate (550 g, 2.2 mol, 1.25 equivalent) was preheated to 100° C. in a 130° C. oil bath. The preheated mixture was removed from the oil bath followed by addition of KF (2.3 g, 0.3% of total weight) all at once. The temperature in the reaction mixture rose to 135° C. in about 5 min and then began dropping. The reaction flask was then returned to the 130° C. oil bath and maintained under stirring at 130° C. for over 2 hours. $^{31}$P NMR indicated that no starting reactants remained. The reaction mixture was then quenched at 130° C. with Ca(OH)$_2$ (1.5 g, half molar equivalent of KF) and maintained under stirring at 130° C. for over 1 hour. By-product phenol was stripped off under full vacuum (80 mTorr) at 115° C. The residue was dissolved in dichloromethane and the CaF$_2$ removed via filtration using a celite pad. Solvent was then stripped under reduced pressure. The resulting highly viscous product (264 g) had an acid number of 0.12 mgKOH/g and 110 ppm of Ca.

The hydroxyl number of this mixture of Compounds (1) and (2) is about 170 and its phosphorus content approximately 17 weight percent.

Examples 3-7

Comparative Examples 1-4

Table 1 below sets forth flexible polyurethane foam-forming compositions (Examples 3-7) containing monohydroxy cyclic phosphonate (I) in accordance with the invention.

TABLE 1

Flexible Polyurethane Foam-forming Compositions (Wt. Parts)

| Component | 2 lb foam Example 3 | 1.5 lb foam Example 4 | 1 lb foam Example 5 | 1 lb foam Example 6 | 1 lb foam Example 7 |
|---|---|---|---|---|---|
| Polyether Polyol (3000 m.w.) | 100 | 100 | 100 | 100 | 100 |
| Flame Retardant Compound (1) from Example 1 | 4 | 4 | 6 | — | 4.2 |
| Mixture of Flame Retardant Compounds (1) and (2) of Example 2 | — | — | — | 4.8 | — |
| t-Butyl triphenyl phosphate | — | — | — | 11.2 | 7.8 |
| Dabco 33LV/A-1 amine catalyst (Air Products) | 0.20 | 0.1 | 0.30 | 0.35 | 0.35 |
| Water (for CO$_2$ production) | 4 | 4 | 5.6 | 5.6 | 5.6 |
| Silicone surfactant L-620 (stabilizer) (General Electric) | 0.8 | 1.3 | 0.7 | 0.8 | 0.9 |
| Stannous octoate catalyst T-10 (Air Products) | 0.23 | 0.3 | 0.3 | 0.25 | 0.3 |
| Toluene diisocyanate (TDI) | 71 | 50.14 | 71 | 71 | 71 |
| NCO Index | 110 | 110 | 110 | 110 | 110 |

Table 2 below sets forth flexible polyurethane foam-forming compositions (Comparative Examples 1-4) containing a commercial dihydroxy phosphonate flame retardant, i.e., Fyrol 6 (diethyl bis(2-hydroxyethyl)aminomethylphosphonate having the structure (HOCH$_2$CH$_2$)$_2$NCH$_2$P(=O)(OCH$_2$CH$_3$)$_2$; CAS 2781-11-5) and/or tert-butylphenyl diphenyl phosphate (CAS 56803-37-3).

TABLE 2

Comparison Flexible Polyurethane Foam-forming Compositions

| Component | Comparative Example 1 | Comparative Example 2 | Comparative Example 3 | Comparative Example 4 |
|---|---|---|---|---|
| Polyether Polyol (3000 m.w.) | 100 | 100 | 100 | 100 |
| Fyrol 6 | 3 | — | — | — |
| t-Butylphenyl diphenyl phosphate | 20 | 20 | — | — |
| Fyrol FR2 | — | — | 16 | 14 |
| Dabco 33LV/A-1 amine catalyst (Air Products) | 0.23 | 0.25 | 0.21 | 0.22 |
| Methylene chloride (blowing agent) | — | — | 10 | — |
| Water (for CO$_2$ production) | 5.6 | 5.6 | 5.6 | 3.55 |
| Silicone surfactant L-620 (General Electric (stabilizer) | 1.0 | 1 | 1 | 0.80 |
| Stannous octoate catalyst T-10 (Air Products) | 0.45 | 0.60 | 0.76 | 0.35 |
| Toluene diisocyanate (TDI) | 71 | 71 | 71 | 47.3 |
| NCO Index | 110 | 110 | 110 | 110 |

Flexible polyurethane foams were obtained from the flexible foam-forming compositions of Tables 1 and 2 employing the following general procedure:

Polyol, flame retardant, methylene chloride blowing agent (used only for a 1 lb/ft$^3$ foam nominal density), water, tin and amine catalysts and stabilizer were mixed with stirring in a first beaker. In a separate beaker, the toluene diisocyanate (TDI) was weighed out. A cardboard box for each foam, dimensions of 16×16×5.5 cubic inches, was provided and the catalysts placed in a syringe. The first beaker was stirred at 2100 revolutions per minute for a period of 35 seconds and then the catalysts were dosed thereto while stirring was continued. After a total of 45 seconds of stirring, the TDI was added to the mixture. Stirring was then continued for an additional 7 seconds and the still-fluid mixture was introduced into the box. Cream time and rise time were recorded. Once a foam ceased to rise, it was allowed to cure for 3 days at room temperature.

The Cal. TB 117A test, a standard flammability test, was employed to evaluate the flame retardancy performance of the flame retardants used in making the foams of Examples 3-7 and the foams of Comparative Examples 2-4. The foam of Comparative Example 1 could not be evaluated due to its severe shrinkage.

The test is a small-scale vertical test with a twelve-second-ignition time. The sample size is 12×3×0.5 cubic inches. The ignition source is removed after twelve seconds. A second clock is started if the sample continues to burn. The criteria for failing includes a sample exceeding an individual burn distance of eight inches or an average burn distance of six inches. The shorter the burn length the better the performance of a given flame retardant.

The results of the flammability test are presented in Table 3 below:

TABLE 3

Results of the Cal. TB 117A Flammability Tests

| | Foam Characteristics | | Cal. TB 117A Test | | |
| --- | --- | --- | --- | --- | --- |
| | | | Initial, average | Aged, average | |
| Example | Air Flow, ft³/min | Density, lb/ft³ | burn distance, in. | burn distance, in | Part D |
| Ex. 3 | 4.0 | 2.0 | 2.0 | 2.1 | pass |
| Ex 4 | 4.5 | 1.5 | 2.6 | 2.9 | pass |
| Ex. 5 | 3.2 | 1.0 | 3.5 | 3.9 | pass |
| Ex. 6 | 4.2 | 1.0 | 2.3 | 2.5 | pass |
| Ex. 7 | 5.6 | 1.0 | 4.2 | 4.5 | pass |
| Comp Ex. 1 | Foam Collapsed | — | — | — | — |
| Comp Ex. 2 | 4.4 | 1.0 | 4.2 | 6.0 | pass |
| Comp Ex. 3 | 5.6 | 1.0 | 4.8 | 4.9 | pass |
| Comp Ex. 4 | 4.3 | 1.8 | 1.7 | 2.2 | pass |

Industry standard Fyrol FR2, tris(dichloroisopropyl)phosphate (CAS 13674-87-8), was used as a reference since it is a very efficient flame retardant; tert-butylphenyl diphenyl phosphate (CAS 56803-37-3) was used as a reference since it was used as part of the flame retardant composition.

Attempts to use Fyrol 6 in flexible polyurethane foam failed due to severe foam shrinkage (Comparative Example 1) owing to the high crosslinking density resulting from the presence of two hydroxyl groups in its molecule.

The foam of Example 5 was subjected to extraction and GC analysis. Compound (1) was not detected indicating that it had completely reacted and become chemically incorporated in the polyurethane foam matrix.

Example 8 and Comparative Example 5

For these examples the flexible polyurethane foam-forming compositions set forth below in Table 4 were utilized:

TABLE 4

Flexible Polyurethane Foam-forming Compositions (Wt. Parts)

| Component | Example 8 | Comparative Example 5 |
| --- | --- | --- |
| Polyether Polyol (3000 m.w.) (Vornal, Dow) | 100 | 100 |
| Flame Retardant Compound (1) of Example 1 | 4.8 | — |
| t-Butylphenyl diphenyl phosphate | 11.2 | 12.8 |
| Diethyl(2-hydroxyethyl)phosphonate (CAS 39997-40-5, disclosed in 2007/0112084) | — | 3.2 |
| Dabco 33LV/A-1 (Air Products) | 0.35 | 0.35 |
| Methylene chloride (blowing agent) | 8 | 8 |
| Water (for CO₂ production) | 5.6 | 5.6 |
| Silicone surfactant L-620 (stabilizer) (General Electric) | 0.8 | 0.8 |
| Toluene diisocyanate (TDI) | 71 | 71 |
| Stannous octoate catalyst T-10 (Air Products) | 0.25 | 0.25 |
| NCO Index | 110 | 110 |

Flexible polyurethane foams were prepared from the foam-forming compositions of Table 4 in substantially the same manner as described supra for Examples 3-7 and Comparative Examples 1-4. The resulting foams were evaluated for scorch employing the LAB Color Scale procedure hereinafter described.

Scorch Evaluation Employing the LAB Color Scale

In 1931, the Commission Internationale d'Eclairage (CIE) developed a color model that displays every color perceived by the human eye. In 1976, this model was updated and refined in order to create the CIE Lab color system. Unlike RGB colors that are screen-dependent and CMYK colors that vary with printer, ink and paper characteristics, CIE Lab colors are device-independent. Therefore, the visual characteristics of these colors remain consistent on monitors, printers and scanners.

Photoshop CS5 software was used to separate "L", "a" and "b" components of high resolution digital images of foam samples taken under standard light conditions.

In Photoshop, the Lab mode consists of three color channels. The first channel is Lightness (L). The Lightness component, otherwise known as luminosity, can range from 0 to 100. A Lightness value of 0 equals black and a value of 100 equals white. Thus, the higher the value, the more vivid the color. The other two channels, "a" and "b", represent color ranges. The "a" channel contains colors ranging from green to red and the "b" channel contains colors ranging from blue to yellow. Positive values of "b" represent yellow color. As in the case with luminosity, the higher the value the more vivid the color. Samples with "b" values of <15 appear white. Samples with values of 20-25 appear off-white to light yellow while samples with b values >30 are noticeably yellow.

The ordinary, casual observer is able to differentiate between two colors that are 2-5 units apart.

Oven foam aging test followed by spectral color analysis was used to determine the scorch potentials of the flexible polyurethane foams of Example 8 and Comparative Example 5. This method evaluates scorch propensity in a sample by measuring the Delta E score as the polyurethane foam sample ages at high temperature. Delta E was measured using the LAB color scale with LAB values of L=90.69, a=−0.05 and b=−0.39.

Samples of the polyurethane foams of Example 8 and Comparative Example 5 were cut from the center and aged at 180° C. for up to 150 minutes and samples were removed for evaluation after 60, 90, 120 and 150 minutes. The time and temperature for the oven aging were balanced to reflect actual foam production scorch performance. Foam samples were photographed and delta E for each sample (in duplicates) calculated. Graphic representation of scorch potential is shown on FIG. 1. Foams with a maximum delta E of about 30 or less after 150 minutes are considered non-scorchy under actual production conditions.

Comparative Examples 6-7

Attempts were made to prepare additional flexible polyurethane foams from the 1 lb foam-forming composition of Comparative Example 5 but employing 8-16 weight parts of dimethyl 2-hydroxyethylphosphonate (CAS 54731-72-5) as the sole flame retardant additive as disclosed in US 2007/0112084 (Comparative Example 6). However, all of the resulting foams collapsed demonstrating the unsuitability of dimethyl 2-hydroxyethylphosphonate as the sole flame retardant for this foam-forming composition. An attempt to utilize a mixture of 12.8 weight parts of t-butyl triphenyl diphenylphosphonate and 3.2 weight parts of dimethyl 2-hydroxyethylphosphonate (Comparative Example 7) as a combination flame retardant additive failed since the latter turned out to be immiscible with the former.

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to any particular embodiment disclosed as the best mode contemplated for carrying out the process of the invention but that the invention will include all embodiments falling within the scope of the appended claims.

The invention claimed is:

1. A monohydroxy cyclic phosphonate of general formula (I):

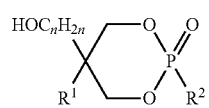

wherein $R^1$ is selected from the group consisting of an alkyl selected from methyl, ethyl, n-propyl, isopropyl, n-butyl, sec-butyl, or tert-butyl; an alkenyl, an aryl; an alkaryl; an aralkyl or an alkoxy group each of up to 10 carbon atoms; a —$CH_2CH_2OR^3$ group; a —$CH_2CH_2C(=O)R^3$ group; or, a —$CH_2CH_2C(=O)OR^3$ group in which each $R^3$ independently is an alkyl, alkenyl, aryl, alkaryl, aralkyl or alkoxy group of up to 10 carbon atoms, and $R^2$ is selected from the group consisting of an alkyl selected from methyl, ethyl, propyl, isopropyl, n-butyl, iso-butyl, sec-butyl, tert-butyl; an aryl; an alkaryl; an aralkyl or an alkoxy group each of up to 10 carbon atoms; a —$CH_2CH_2OR^3$ group; a —$CH_2CH_2C(=O)R^3$ group; or, a —$CH_2CH_2C(=O)OR^3$ group, where $R^3$ is as defined; provided that when $R^2$ is any of ethyl, isopropyl, n-butyl or iso-butyl, $R^1$ is other than ethyl, and n is 1 to 8, monohydroxy cyclic phosphonate (I) being substantially free of polyhydroxy phosphonate and containing a phosphorus content of 8 weight percent or greater.

2. Monohydroxy cyclic phosphonate (I) of claim 1 which is at least one compound selected from the group consisting of:
1,3,2-dioxaphosphorinane-5-methanol, 5-ethyl-2-(2-methyl)-, 2-oxide; 1,3,2-dioxaphosphorinane-5-methanol, 5-methyl-2-(2-methylpropyl)-, 2-oxide; 1,3,2-dioxaphosphorinane-5-methanol, 5-propyl-2-(n-butyl)-, 2-oxide;
1,3,2-dioxaphosphorinane-5-ethanol, 5-methyl-2-phenyl-, 2-oxide;
1,3,2-dioxaphosphorinane-5-propanol, 5-butyl-2-phenyl-, 2-oxide;
1,3,2-dioxaphosphorinane-5-propanol, 5-ethyl-2-benzyl-, 2-oxide;
1,3,2-dioxaphosphorinane-5-propanol, 5-methyl-2-p-tolyl-, 2-oxide;
1,3,2-dioxaphosphorinane-5-methanol, 5-ethyl-2-methoxyethyl-, 2-oxide;
1,3,2-dioxaphosphorinane-5-methanol, 5-ethyl-2-acetoxyethyl-, 2-oxide;
1,3,2-dioxaphosphorinane-5-methanol, 5-ethyl-2-methoxypropanoxycarbonyl-, 2-oxide;
1,3,2-dioxaphosphorinane-5-methanol, 5-methoxyethyl-2-(2-methyl)-, 2-oxide; and,
1,3,2-dioxaphosphorinane-5-methanol, 2,5-dimethoxyethyl-, 2-oxide.

3. A flame retardant composition comprising at least one monohydroxy cyclic phosphonate (I) of claim 1 and at least one other phosphorus-containing flame retardant which is not a polyhydroxy phosphonate.

4. The flame retardant composition of claim 3 wherein the at least one other phosphorus-containing flame retardant is at least one member selected from the group consisting phosphoric acid, 4-tert-butylphenyl diphenyl phosphate, tert-butylphenyl diphenyl phosphate and isopropylphenyl diphenyl phosphate.

5. A flame retardant composition comprising at least one monohydroxy cyclic phosphonate (I) of claim 1 in admixture with at least one dicyclic phosphonate of general formula (II):

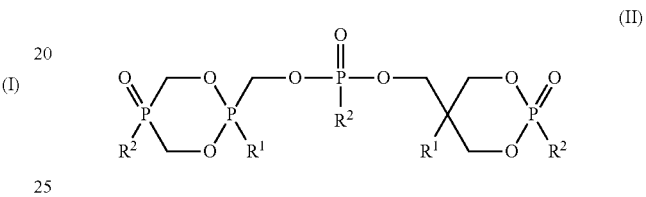

wherein $R^1$ and $R^2$ each independently has one of the aforestated meanings and, optionally, in further admixture with at least one other phosphorus-containing flame retardant which is not polyhydroxy phosphonate.

6. The flame retardant composition of claim 5 wherein the at least one other phosphorus-containing flame retardant is at least one member selected from the group consisting phosphoric acid, 4-tert-butylphenyl diphenyl phosphate, tert-butylphenyl diphenyl phosphate and isopropylphenyl diphenyl phosphate.

7. The flame retardant composition of claim 3 containing 8.0 weight percent or greater phosphorus content based on the total weight of phosphorus-containing flame retardant compound(s) in the composition.

8. The flame retardant composition of claim 4 containing 8.0 weight percent or greater phosphorus content based on the total weight of phosphorus-containing flame retardant compound(s) in the composition.

9. The flame retardant composition of claim 5 containing 8.0 weight percent or greater phosphorus content based on the total weight of phosphorus-containing flame retardant compound(s) in the composition.

10. The flame retardant composition of claim 6 containing 8.0 weight percent or greater phosphorus content based on the total weight of phosphorus-containing flame retardant compound(s) in the composition.

11. A flame retardant flexible polyurethane foam obtained from a flexible polyurethane foam-forming composition which includes a flame retardant-effective amount of a flame retardant composition containing at least one monohydroxy cyclic phosphonate (I) of claim 1.

12. A flame retardant flexible polyurethane foam obtained from a polyurethane foam-forming composition which includes a flame retardant-effective amount of a flame retardant composition containing at least one monohydroxy cyclic phosphonate (I) of claim 2.

13. A flame retardant flexible polyurethane foam obtained from a polyurethane foam-forming composition which includes a flame retardant-effective amount of a flame retardant composition of claim 3.

14. A flexible polyurethane foam obtained from a polyurethane foam-forming composition which includes a flame retardant-effective amount of a flame retardant composition of claim 4.

15. A flexible polyurethane foam obtained from a polyurethane foam-forming composition which includes a flame retardant-effective amount of a flame retardant composition of claim 5.

16. A flexible polyurethane foam obtained from a polyurethane foam-forming composition which includes a flame retardant-effective amount of a flame retardant composition of claim 6.

17. A flexible polyurethane foam obtained from a polyurethane foam-forming composition which includes a flame retardant-effective amount of a flame retardant composition of claim 7.

18. A flexible polyurethane foam obtained from a foam-forming reaction composition which includes a flame retardant-effective amount of a flame retardant composition of claim 8.

19. A flexible polyurethane foam obtained from a foam-forming reaction composition which includes a flame retardant-effective amount of a flame retardant composition of claim 9.

20. A flexible polyurethane foam obtained from a foam-forming reaction composition which includes a flame retardant-effective amount of a flame retardant composition of claim 10.

21. A process for making monohydroxy cyclic phosphonate (I) of claim 1 which comprises reacting at least one diaryl phosphonate of general formula (III):

wherein each $R^2$ has one of the aforestated meanings with at least one trihydroxylalkyl alcohol of general formula (IV):

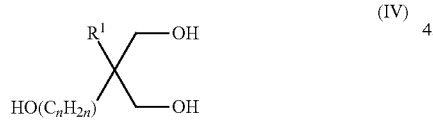

wherein $R^1$ has one of the aforestated meanings and each n independently is 1 to 10 to provide monohydroxy cyclic phosphonate (1).

22. The process of claim 21 wherein $R^1$ and $R^2$ each independently is selected from the group consisting of methyl, ethyl, propyl, isopropyl, n-butyl, tert-butyl and phenyl and n is 1 to 4.

23. The process of claim 21 wherein diaryl phosphonate (III) is at least one compound selected from the group consisting of diphenylmethylphosphonate, diphenylphenylphosphonate, diphenylethylphosphonate, diphenylbutylphosphonate and diphenyl-iso-butylphosphonate, and trihydroxy alcohol (IV) is at least one compound selected from the group consisting of 1,3-propanediol, 2-ethyl-2-(hydroxymethyl), 1,3-propanediol, 2-phenyl-2-(hydroxymethyl), 1,3-propanediol, 2-ethyl-2-(hydroxybutyl), $CH_3OCH_2CH_2C(CH_2OH)_3$, $CH_3OCH_2CH_2C(CH_2OH)_2CH_2CH_2OH$, $CH_3C(=O)OCH_2CH_2C(CH_2OH)_3$, $CH_3C(=O)OCH_2CH_2C(CH_2OH)_2CH_2CH_2OH$, $CH_3C(=O)CH_2CH_2C(CH_2OH)_3$, $CH_3C(=O)CH_2CH_2C(CH_2OH)_2CH_2CH_2OH$, and mixtures thereof.

24. The process of claim 21 wherein the reaction of diaryl phosphonate (III) with dihydroxyalkyl alcohol (IV) is carried out within an inert polar aprotic organic solvent.

25. The process of claim 21 wherein at least one dicyclic phosphonate of the general formula (II):

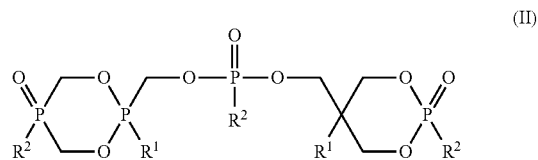

wherein $R^1$ and $R^2$ each independently has one of the aforestated meanings is co-produced in admixture with monohydroxy cyclic phosphonate (I) and, optionally, monohydroxy cyclic phosphonate (I) is separated from its admixture with the at least one dicyclic phosphonate (II).

26. The process for making monohydroxy cyclic phosphonate (I) of claim 1 wherein $R^2$ is a $-CH_2CH_2OR^3$ group, a $-CH_2CH_2C(=O)R^3$ group or a $-CH_2CH_2C(=O)OR^3$ group, which comprises:

a) reacting at least one trihydroxylalkyl alcohol of general formula (IV):

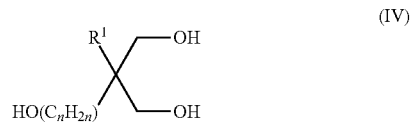

wherein $R^1$ has one of the aforestated meanings and each n independently is 1 to 10, with at least one dialkyl phosphite of general formula $(R^4O)_2P(=O)H$ (V) in which each $R^4$ independently is an alkyl group of from 1 to 4 carbon atoms to provide monohydroxy cyclic phosphite of the general formula; and,

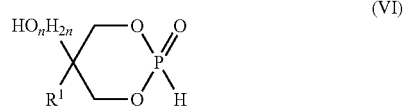

b) reacting monohydroxy cyclic phosphite (VI), optionally, in substantially pure form, with at least one of $CH_2=CH-C(=O)OR^3$, $CH_2=CH-OC(=O)R^3$ or $CH_2=CH-OR^3$ wherein $R^3$ has one of the aforestated meanings, to provide monohydroxy cyclic phosphonate (I).

* * * * *